(12) United States Patent
Schmidt-Ott et al.

(10) Patent No.: US 10,722,287 B2
(45) Date of Patent: Jul. 28, 2020

(54) SPARK ABLATION DEVICE

(71) Applicant: VSParticle Holding B.V., Delft (NL)

(72) Inventors: Andreas Schmidt-Ott, Delft (NL); Tobias Vincent Pfeiffer, Delft (NL)

(73) Assignee: VSPARTICLE HOLDING B.V., Delft (NL)

( * ) Notice: Subject to any disclaimer, the term of this patent is extended or adjusted under 35 U.S.C. 154(b) by 1444 days.

(21) Appl. No.: 14/447,143

(22) Filed: Jul. 30, 2014

(65) Prior Publication Data

US 2015/0080877 A1 Mar. 19, 2015

Related U.S. Application Data

(63) Continuation of application No. PCT/NL2013/050049, filed on Jan. 29, 2013.

(30) Foreign Application Priority Data

Jan. 31, 2012 (NL) .................................... 2008208

(51) Int. Cl.
- *A61B 18/12* (2006.01)
- *H01J 37/32* (2006.01)
- *B22F 1/00* (2006.01)
- *A61B 18/00* (2006.01)

(52) U.S. Cl.
CPC .... *A61B 18/1206* (2013.01); *H01J 37/32055* (2013.01); *H01J 37/32064* (2013.01); *A61B 2018/00577* (2013.01); *A61B 2018/00702* (2013.01); *B22F 1/0018* (2013.01)

(58) Field of Classification Search
CPC ...... A61B 18/1206; A61B 2015/00702; A61B 2015/00994; H01J 37/32055; H01J 37/32064

See application file for complete search history.

(56) References Cited

U.S. PATENT DOCUMENTS

| | | |
|---|---|---|
| 4,645,895 A | 2/1987 | Boxman et al. |
| 2001/0003272 A1 | 6/2001 | Schmitt et al. |
| 2003/0230554 A1 | 12/2003 | Schroder et al. |
| 2005/0034668 A1 | 2/2005 | Garvey et al. |
| 2005/0061785 A1 | 3/2005 | Schroder et al. |
| 2008/0143260 A1 | 6/2008 | Tuymer et al. |
| 2008/0166500 A1 | 7/2008 | Byeon et al. |

FOREIGN PATENT DOCUMENTS

WO 2013/115644 8/2013

OTHER PUBLICATIONS

Schwyn, "Aerosol Generation by Spark Discharge", Journal of Aerosol Science vol. 19, Issue 5, 1988, 639-642.

*Primary Examiner* — Michael F Peffley
*Assistant Examiner* — Samantha M Good
(74) *Attorney, Agent, or Firm* — Peacock Law P.C.; Janeen Vilven; Justin Muehlmeyer

(57) ABSTRACT

A spark ablation device for generating nanoparticles comprising a spark generator; the spark generator comprising first and second electrodes, wherein the spark generator further comprises at least one power source which is arranged to be operative at a first energy level for maintaining a discharge between the first and second electrodes, which power source is arranged for repetitively increasing the energy of the discharge to a predetermined secondary level that is higher than the first energy level for ablating a portion of the electrodes.

10 Claims, 1 Drawing Sheet

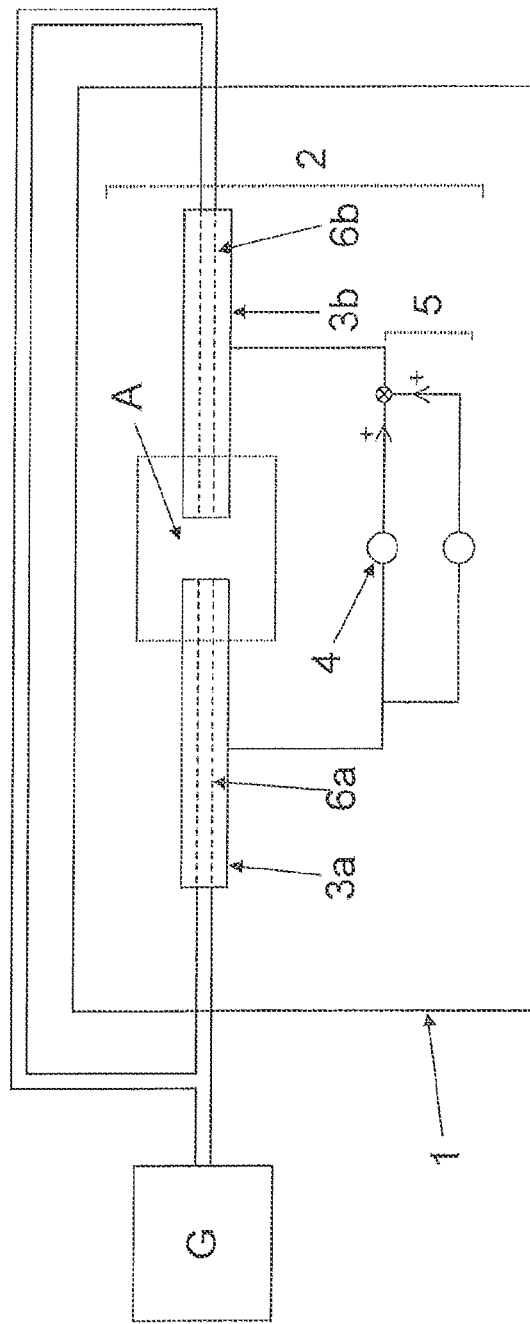

SPARK ABLATION DEVICE

CROSS-REFERENCE TO RELATED APPLICATIONS

This application is a continuation application of Patent Cooperation Treaty Application No. PCT/NL2013/050049, entitled "Spark Ablation Device", filed on Jan. 29, 2013, which claims priority to Netherlands Patent Application No. 2008208, filed on Jan. 31, 2012, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention relates to a spark ablation device and to a method for generating nanoparticles.

Description of Related Art

Ablation devices based on electrode vaporization by spark discharge are known in the prior art; see, e.g., S. Schwyn et al., J. Aerosol Sci., 1988, 19 (5), 639. The spark generator of such devices typically comprises a power source, an RLC circuit (i.e., a circuit comprising a resistor, an inductor and a capacitor) and a pair of electrodes. The capacitor is continually charged by the power source; when the breakdown voltage is reached, discharge occurs between the electrodes. The spark discharge is repetitive, and between sparks there is no discharge. Components and conditions are chosen such that the energy of the discharge is sufficient to cause electrode ablation. Electrode ablation is the evaporation/vaporization of the electrode through the presence of plasma, i.e., as a result of heating and ion bombardment. The power of the discharge is the product of voltage and current.

Disadvantages of state of the art devices and methods for spark ablation are: (a) their limited nanoparticle production rates: typical maximum production rates are in the range of milligrams per hour, due to the low spark repetition frequencies of conventional spark generator circuits; (b) as the frequency is increased local heating of the electrodes occurs as subsequent sparks hit the same point on the electrode surface; this leads to emission of (relative to nanoparticles) large particles formed from dispersions of melted material; and (c) above a certain frequency, discharge becomes continuous and particle generation stops or desired particle characteristics are lost.

Each of US2005/034668 and US2008/166500 disclose a spark ablation device for generating nanoparticles comprising a spark generator; the spark generator comprising first and second electrodes and at least one power source which is arranged to be operative for maintaining a discharge between the first and second electrodes. A spark generator is an electrical circuit arranged for generating sparks between electrodes of the spark generator. In the device of US2005/034668 the electrodes are hollow and connected to a gas supply. Further in this device a ring shaped electromagnet is applied providing a magnetic field in the discharge area between the first and second electrodes. Since in such a ring shaped electromagnet the magnetic field lines pass through in parallel with the core axis of the magnet, the magnetic field lines in US2005/034668 are predominantly parallel with the electrical field lines that entertain the discharge.

BRIEF SUMMARY OF THE INVENTION

It is an object of the invention to provide a spark ablation device and method which overcome one or more problems of the devices and methods of the prior art. Spark ablation involves applying electrical energy to create sparks between pairs of electrodes. Electrode material is vaporized at the electrode or electrodes from which each high-energy spark originates. Under suitable conditions, nanoparticles are formed from the vaporized material. Nanoparticles as understood in this application are particles having a diameter up to a maximum of about 1 μm.

Further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawing, which is incorporated into and forms a part of the specification, illustrates one or more embodiments of the present invention and, together with the description, serves to explain the principles of the invention. The drawing is only for the purpose of illustrating one or more preferred embodiments of the invention and is not to be construed as limiting the invention. In the drawings:

FIG. 1 shows a spark ablation device according to the invention.

DETAILED DESCRIPTION OF THE INVENTION

In a first aspect, the invention relates to a spark ablation device for generating nanoparticles comprising a spark generator; the spark generator comprising first and second electrodes and at least one power source which is arranged to be operative for maintaining a discharge between the first and second electrodes, which power source is configured for repetitively varying its power output between a first energy level and a second energy level to arrange that a substantially continuous discharge is maintained between the electrodes of the spark ablation device at the first energy level, and wherein the energy level of the discharge is intermittently increased from said first energy level to a second energy level higher than the first energy level for ablating at least a portion of the electrodes.

Providing an at least substantially continuous discharge or simmer discharge between the electrodes and superimposing a pulsed discharge thereover results in a number of advantages: (i) lower voltages can be applied as the break-down voltage between the electrodes does not have to be reached; (ii) each spark has the same "starting" conditions, thus constant particle characteristics and a narrow distribution of particle sizes can be achieved; (iii) very short, high power discharge pulses are possible, but with the average power being low enough to avoid cooling problems; (iv) sufficiently high pulse energies can be used to allow simultaneous evaporation of materials of different boiling points wherein the electrodes are sintered electrodes; (v) the RLC circuits commonly applied allow repetition frequencies up to only 1000 Hz, whereas for the method and device of the present invention this limit is not applicable and thus much higher nanoparticle production rates are possible, such as at least a factor of 10 greater; (vi) for most electrode arrangements, the position where the simmer discharge meets the electrodes fluctuates; subsequent sparks do not strike repetitively at the same point on the electrodes which would otherwise lead to non-even evaporation and formation of liquid pools and therewith large particles, and; (vii) the average electric field in the spark generator is smaller than with conventional circuits, because the otherwise required break-down voltage between the electrodes does not need to be reached. This reduces particle loss by electrostatic precipitation.

It is possible to implement the functionality of the spark ablation device such that only a single power source is needed. In a preferred embodiment however, the at least one power source comprises a pulse generator for repetitively increasing the energy of the discharge. Various examples of suitable pulse generators are known to a person of skill in the art.

Secondly, the at least one power source can comprise a continuous DC power source or a continuous AC power source, supplemented with pulsed power from the same or another power source. The continuous power source may comprise one or more elements that can store electrical energy, such as a capacitor or a coil. The pulsed power source has the function of periodically supplying energy for the production of nanoparticles as well as periodically providing recharging energy for the said elements that can store electrical energy. Preferably the at least one power source is selected to be (a) a current source, or (b) a voltage source.

In a further preferred embodiment, the spark ablation device further comprises an ignition circuit for initial ignition of the continuous discharge.

In a second aspect, the first and/or second electrodes are preferably hollow and are further preferably connected or connectable to a gas supply.

Hollow electrodes, in particular electrodes that are connected or are connectable to a gas supply, are advantageous since they allow the addition or removal of reactants or products, e.g., nanoparticles once formed may be removed via one or both of the electrodes. The gas flow can be held at a temperature providing effective cooling of the electrodes to avoid heating problems. The tube shape of the electrodes provides an additional advantage when combined with a magnetic field, as described below, because the resulting toroidal gap allows spinning of the discharge within this torus.

According to US2005/034668 the spark generator may comprise means to provide a magnetic field in a discharge area between the first and second electrodes. In this known device the magnetic field lines are predominantly parallel to the electrical field lines.

In a third aspect of the invention the means to provide a magnetic field provide a magnetic field with field lines that are substantially perpendicular to the electrical field lines that cause the discharge between the electrodes, so as to influence the location on the first and second electrodes at which discharge occurs. It is possible that the magnetic field lines of the magnetic field are oriented oblique with respect to the electrical field lines between the electrodes, provided that there is a notable component of these field lines that are substantially perpendicular to the electrical field lines causing the discharge between the electrodes.

Through providing a magnetic field with magnetic field lines that are at least in part predominantly perpendicular to the electrical field lines, the position at which the continuous discharge meets the electrodes is constantly varied. This results in the pulsed discharges occurring at different positions and ensures a more even electrode evaporation. Wherein the electrodes are hollow (tube-shaped) and the spark generator comprises means to provide said magnetic field relative to the first and/or second electrodes, this advantageously permits spinning of the discharge.

The means to provide a magnetic field may be either a permanent magnet or magnets, an electric magnet or magnets, or a combination thereof.

Wherein the means for providing a magnetic field are embodied as electric magnets, this allows the magnetic field to be switched on only during certain periods in each cycle. The magnetic field can then for example be switched off during the pulse discharges so as to prevent them from being disturbed thereby. Permanent magnets constitute a mechanically simpler solution.

In a fourth aspect, the invention relates to a method for generating nanoparticles with a spark ablation device comprising electrodes for providing sparks by repetitively providing pulsed energy to the electrodes, wherein a substantially continuous discharge is maintained between the electrodes of the spark ablation device, the energy level of which discharge is intermittently increased from a first energy level to a second energy level higher than the first energy level for ablating a portion of the electrodes.

The invention will hereafter be further elucidated with reference to the drawing of FIG. 1 showing schematically an example of a spark ablation device according to the invention. It should be appreciated that this example is provided for illustrative purposes only and is not to be considered limiting of the invention.

With reference to the drawing, FIG. 1 shows a spark ablation device 1 for generating nanoparticles comprising a spark generator 2; nanoparticles are generated in the region A. It is remarked that although not specifically shown, the device also includes an outlet for the generated nanoparticles.

The spark generator comprising first and second electrodes 3a,3b, and the spark generator 2 further comprises at least one power source 4 which is arranged to be operative at a first energy level for maintaining a discharge between the first and second electrodes 3a,3b. The power source 4 is configured for repetitively varying its power output between a first energy level and a second energy level to arrange that a substantially continuous discharge is maintained between the electrodes 3a,3b of the spark ablation device 1 at the first energy level. The energy level of the discharge is intermittently increased from said first energy level to a second energy level higher than the first energy level for ablating at least a portion of the electrodes 3a,3b.

For repetitively increasing the energy of the discharge the at least one power source 4 preferably comprises a pulse generator 5. The at least one power source 4 comprises for instance a continuous DC power source and/or a continuous AC power source, supplemented with a source for pulsed power, wherein preferably the at least one power source is selected to be either (a) a current source, or (b) a voltage source.

According to the second aspect of the invention, the first and second electrodes 3a,3b are hollow, i.e., they are provided with conduits 6a,6b running the length of each electrode 3a,3b, and connected to a gas supply G. Also an (additional) inlet/outlet for the gas will be present. Such an arrangement allows the addition or removal of reactants or products, e.g., nanoparticles once formed may be removed via one or both of the electrodes 3a,3b. One or more additional gas flows into and/or out of zone A may further be provided for the same purpose, either in combination, or as an alternative to providing hollow electrodes.

According to one of the aspects of the invention, the spark ablation device 1 comprises means to provide a magnetic field (not shown) arranged relative to the first and second electrodes 3a,3b to influence the location on the electrodes 3a,3b at which the discharge occurs. The means to provide a magnetic field provide a magnetic field with field lines preferably substantially perpendicular to the discharge.

The magnets could be embodied as rings around the electrodes. Permanent ring-shaped or tube-shaped magnets magnetized in the direction of the axis of the electrodes are suitable. Alternatively, electrical coils providing a magnetic field could be used and positioned accordingly. To ensure a perpendicular component of the magnetic field where the spark is, the poles of the opposed magnets at the location of the electrodes should have opposite polarity. The manner in which this may be implemented is clear for the person skilled in the art and requires no further elucidation with reference to a drawing.

It is expressly pointed out that the inventive merit that is embodied in the invention is exclusively determined by the appended claims. In connection therewith the claims should not be deemed limited to merely the provided schematic example of an embodiment of the invention. On the contrary, the discussed embodiment merely serves to elucidate possible ambiguities in the claims without intention to restrict the scope of protection of the claims to this embodiment only.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A spark ablation device for generating nanoparticles comprising:
   an outlet for the generated nanoparticles; and
   a spark generator comprising first and second electrodes, the spark generator comprising at least one power source which is arranged to be operative for maintaining a discharge between the first and second electrodes, wherein the at least one power source comprises a continuous DC or AC power source and a source for pulsed power, and wherein the at least one power source is configured for repetitively and intermittently varying its power output between a first energy level and a second energy level, wherein the first energy level maintains the discharge substantially continuously between the electrodes of the spark ablation device and the first energy level is insufficient to cause ablation of the electrodes, and the second energy level is higher than the first energy level and sufficient to cause ablation of the electrodes.

2. A spark ablation device according to claim 1, wherein the source for pulsed power comprises a pulse generator for repetitively increasing the energy of the discharge.

3. A spark ablation device according to claim 1, wherein the first energy level is selected at a level insufficient to generate the nanoparticles.

4. A spark ablation device according to claim 1, wherein the second energy level is selected at a level to unavoidably generate the nanoparticles.

5. A spark ablation device according to claim 1, wherein the at least one power source comprises (a) a current source, or (b) a voltage source.

6. A spark ablation device according to claim 1, wherein the spark ablation device comprises an ignition circuit for initial ignition of the discharge.

7. A spark ablation device according to claim 1, wherein the first and/or second electrodes are hollow.

8. A spark ablation device according to claim 7, wherein the first and/or second electrode(s) are connected or connectable to a gas supply.

9. A spark ablation device according to claim 1, wherein the spark generator further comprises means to provide a magnetic field in a discharge area between the first and second electrodes, wherein the means to provide a magnetic field provide a magnetic field with field lines substantially perpendicular to the electrical field lines causing the discharge between the electrodes so as to influence the location on the first and second electrodes at which the discharge occurs.

10. A spark ablation device according to claim 9, wherein the electrodes are provided with magnets or electrical coils to provide the magnetic field lines.

* * * * *